United States Patent
Itagi et al.

(10) Patent No.: US 9,557,278 B1
(45) Date of Patent: Jan. 31, 2017

(54) ELECTROMAGNETIC SEED SENSOR ASSEMBLY FOR SEED TUBE PLANTING APPLICATIONS

(71) Applicant: TSI, Incorporated, Shoreview, MN (US)

(72) Inventors: Amit V. Itagi, Hugo, MN (US); Bernard Wiwel, Shoreview, MN (US); Russell F. Oberg, Beldenville, WI (US)

(73) Assignee: TSI INCORPORATED, Shoreview, MN (US)

( * ) Notice: Subject to any disclaimer, the term of this patent is extended or adjusted under 35 U.S.C. 154(b) by 636 days.

(21) Appl. No.: 13/827,677

(22) Filed: Mar. 14, 2013

Related U.S. Application Data

(60) Provisional application No. 61/698,131, filed on Sep. 7, 2012.

(51) Int. Cl.
*G01N 22/00* (2006.01)
*G01N 27/22* (2006.01)

(52) U.S. Cl.
CPC .............. *G01N 22/00* (2013.01); *G01N 27/22* (2013.01)

(58) Field of Classification Search
CPC ................................ G01N 22/00; G01N 27/22
See application file for complete search history.

(56) References Cited

U.S. PATENT DOCUMENTS

| | | | |
|---|---|---|---|
| 4,239,010 A | 12/1980 | Amburn | |
| 4,246,469 A * | 1/1981 | Merlo | G06M 1/108 111/903 |
| 4,257,001 A | 3/1981 | Partain et al. | |
| 4,268,825 A | 5/1981 | Kaplan | |
| 4,369,404 A | 1/1983 | Flygare et al. | |
| 4,710,757 A | 12/1987 | Haase | |
| 4,782,282 A * | 11/1988 | Bachman | A01C 7/105 324/668 |
| 5,323,721 A | 6/1994 | Tofte et al. | |
| 5,383,353 A | 1/1995 | Marrelli et al. | |
| 5,533,458 A | 7/1996 | Bergland et al. | |
| 5,644,244 A * | 7/1997 | Marrelli | G01N 22/00 324/637 |
| 5,808,242 A | 9/1998 | Satake et al. | |
| 5,880,376 A | 3/1999 | Sai et al. | |
| 5,963,139 A | 10/1999 | Littke | |
| 5,986,553 A | 11/1999 | Young | |
| 6,173,616 B1 | 1/2001 | Tomita | |

(Continued)

OTHER PUBLICATIONS

Riddle et al., "Complex Permittivity Measurements of Common Plastics Over Variable Temperatures", Mar. 2003, vol. 51, pp. 727-733.*

*Primary Examiner* — Jermele M Hollington
*Assistant Examiner* — Haidong Zhang
(74) *Attorney, Agent, or Firm* — Kagan Binder, PLLC

(57) ABSTRACT

Seed sensors that surround the conventional mounting location on existing seed tubes. The seed sensors sense seeds using electromagnetic fields, including RF and microwave fields. In one embodiment, a first seed sensor has a coaxial Fabry-Perot resonant cavity which is formed between two coaxial portions of a conduit that surround the seed tube. Another seed sensor uses a capacitive design. In one embodiment, the driving signals are applied 180 degrees out of phase. The detected phase shift between the reference and reflected signals provides reliable seed counting. Electronics extract the signal from the sensing field.

4 Claims, 18 Drawing Sheets

(56) References Cited

U.S. PATENT DOCUMENTS

| | | |
|---|---|---|
| 6,208,255 B1 | 3/2001 | Conrad et al. |
| 6,346,888 B1 * | 2/2002 | Conrad ................. A01C 7/105 |
| | | 111/903 |
| 6,386,128 B1 | 5/2002 | Svoboda et al. |
| 6,865,956 B2 | 3/2005 | Yamamoto |
| 7,415,892 B2 | 8/2008 | Lam |
| 7,482,818 B2 * | 1/2009 | Greenwald ......... A61M 1/3626 |
| | | 324/639 |
| 7,717,048 B2 | 5/2010 | Peterson, Jr. et al. |
| 7,956,601 B2 | 6/2011 | Becker et al. |
| 8,061,217 B2 | 11/2011 | Hisada et al. |
| 8,074,586 B2 | 12/2011 | Garner et al. |
| 8,136,412 B2 | 3/2012 | Yamamoto et al. |
| 8,350,689 B2 | 1/2013 | Mariman et al. |
| 2012/0169353 A1 | 7/2012 | Sauder et al. |

\* cited by examiner

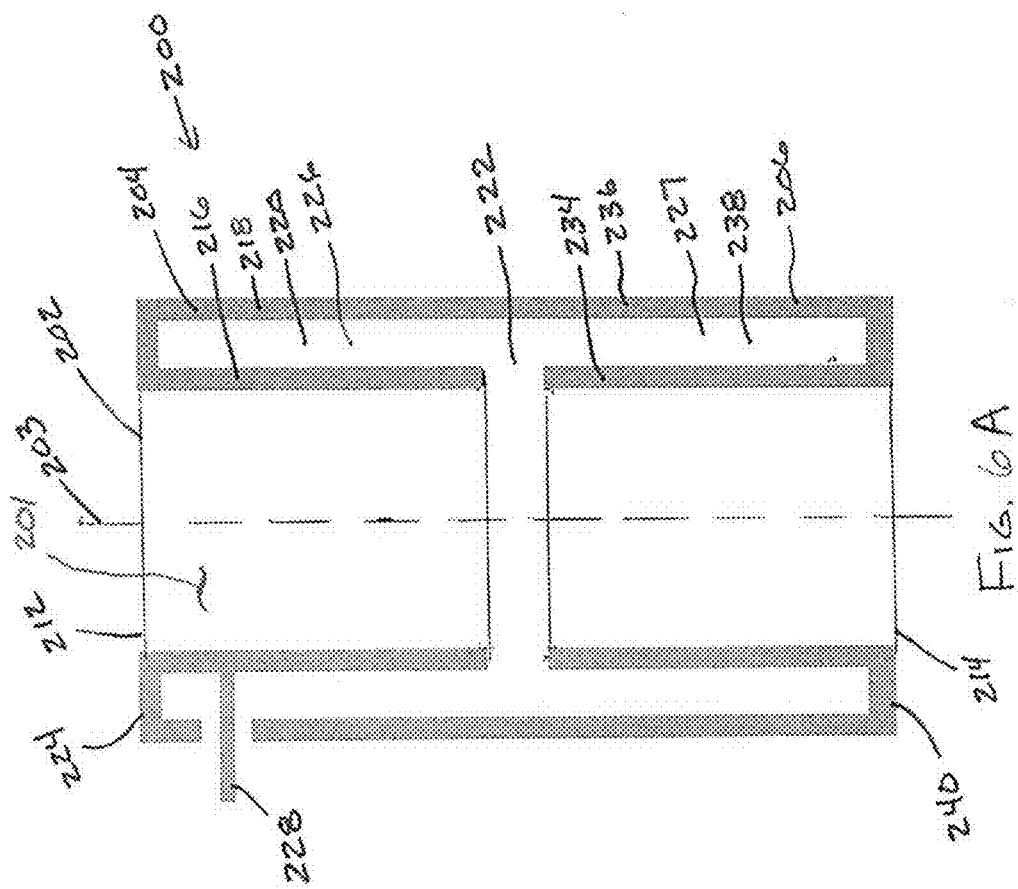

ELECTROMAGNETIC SEED SENSOR ASSEMBLY FOR SEED TUBE PLANTING APPLICATIONS

RELATED APPLICATION

The present application claims the benefit of U.S. Provisional Application No. 61/698,131 filed Sep. 7, 2012, which is incorporated herein in its entirety by reference.

TECHNICAL FIELD

This application relates to seed planters and specifically to seed sensing devices for sensing and counting seeds during a planting operation.

BACKGROUND

As is known in the art, a field seed planter includes a group of seed chutes or seed discharge tubes, one for each row to be simultaneously planted. Each of these seed chutes or tubes convey individual seeds from a seed dispenser in conjunction with a hopper or other seed supply to individual furrows formed in the ground by the planter as it moves across a field. Various monitoring and counting arrangements have been utilized for obtaining a count of the number of seeds dispensed by such seed planters. Such counting is particularly useful in determining and controlling the density or population of seeds planted in order to optimize crop yield. Additionally, seed spacing information is of interest because yield is positively affected by the uniform spacing of such seeds.

One type of seed planter generally utilizes photoelectric devices to sense the passage of individual seeds through the seed chutes or tubes. Such arrangements generally include a light source such as a light emitting diode (LED) positioned to one side of the seed chute or tube and a light responsive element such as a photoresponsive transistor or photovoltaic cell positioned at the opposite side of the tube. Hence, the photoresponsive element normally produces a steady state signal level in response to the light incident thereupon from the light source. As a seed passes through the chute and comes between the light source and light responsive element, the level of light incident upon the light responsive element momentarily decreases. Responsively, the light responsive element produces a momentary change in the normal or steady state signal level output, which represents potentially a seed.

However, various challenges to accuracy of seed counting are encountered including considerable dirt, dust and the like as the planter moves through the field. As the seeds move through the chute, the density of seeds can also result in more of a flow of seeds and not a one-by-one feed and photoresponsive systems may not accurately detect and count a flow of seeds. Moreover, various coatings are commonly provided on seed grains, and these coatings often accumulate in the seed chutes or tubes. Accordingly, the foregoing accumulations of material in the seed tube tend to interfere with proper operation of the photoresponsive system.

Another type of seed sensor utilizes microwave energy. This type of sensor provides a waveguide intersecting a portion of the path of travel of seeds for supporting the propagation of a standing wave pattern of microwave energy. Generally speaking, this apparatus detects disturbances in this standing wave pattern due to the passage of seeds through the seed channel, and in particular through the portion thereof in which the waveguide is located. Associated circuitry is responsive to these disturbances or changes in microwave energy in the waveguide for determining the presence or absence of seeds, as well as in some instances for counting the seeds. One such microwave seed sensor apparatus is shown for example in U.S. Pat. No. 4,246,469 to Merlo, and another such microwave seed sensing apparatus is shown in U.S. Pat. No. 4,239,010 to Amburn.

This type of technology generally makes use of the dielectric properties of seeds and/or other material or articles flowing along a path of travel to provide for detection of such seeds, material or other articles. Generally speaking, an electromagnetic field is set up transversely of the path of travel, such as in the seed chute or channel and detects changes in the electromagnetic field due to the passage of such seeds or other discrete articles or the flow of material therethrough. More particularly, in a case of seeds or articles or materials having measurable dielectric properties, a sensor having primarily capacitive or capacitance-like properties, at a low frequency, may be utilized such as a pair of conductive plates being placed on either side of the path of travel in a seed tube. These plates generally define plates of a capacitor with the seed channel portions therebetween comprising the dielectric portion of the capacitor. Hence, if an object or material of a different relative permittivity or dielectric property relative to air enters this field, the electric field state will be altered. The resulting alteration can be separated into both a transient effect and steady state effect where the transient effect is generally much less pronounced than the steady state effect and of much shorter time duration.

Existing RF sensors suffer from low signal to noise ratio thus limiting sensitivity to small seeds. Existing RF sensors do not use differential detection or phase sensing of the reflected signal.

Some of these seed counting systems, although somewhat reliable, may still encounter challenges with relatively small seeds such as Milo and high seed rate seeds such as soybeans, with overlapping seeds such as Hilldrop Cotton, or with dealing with dust and distinguishing it from the seeds.

SUMMARY

In one example embodiment, an electromagnetic sensor, such as a RF or microwave sensor, is disclosed that fits the conventional mounting location on existing seed tubes but still provide improved performance over the current production sensors by providing two designs (and their variations) for seed sensing using radio frequency (RF) or microwave electromagnetic fields. There is also disclosed herein electronics to extract the signal from the sensing. A result of such an arrangement is to improve seed resolution and to reduce seed spatial variability within the seed tube.

Various embodiments of the invention utilize Fabry-Perot cavities, phase differential driving signals, differential detection or a one port detection, and sense the phase response of the reflected signal for improved sensitivity over state-of-the-art RF sensing. Experimentation with prototypes of these devices, using various combinations of the configurations and technologies, has shown detectability of very small seeds with very little amplification or signal processing.

Other electromagnetic cavities have been proposed for seed sensing before, however, in those sensors, the seed goes through the electromagnetic cavity. In the present invention, the seed goes through a fringing field of an external cavity. Depending on the coupling of the external feed to the resonator, it is possible to get under coupling, critical coupling, or over coupling. The nature of the coupling can be changed by using external tuning elements such as stubs or lumped elements. Such an approach also changes the Q of the resonance. The depicted embodiments of the invention have cut-off regions that suppress radiation out of the open ends of the sensor. This suppression can be further enhanced by coating the surface of the cut-off region with a lossy material. An example of a lossy material is foam impregnated with magnetic or carbon particles, or a ferrite material.

In other embodiments, a RF capacitance (RFC) design is utilized and is unique in that each electrode is provided with a driving signal where the driving signals are 180° out-of-phase with each other thus creating an alternating electric field. The electric field generates a substantially uniform sheet of RF near field within the seed tube. Full planar coverage of the passageway is provided by the electric field intensity so that any seed passing through the plane will be detected. Cut off waveguides on both sides of the sensing plane forces confinement and prevents radiation of a strong oscillating electric field generated between the electrodes The driving voltage of the capacitive design is not directly applied between the two electrodes. Each electrode is excited by a separate RF signal. Each electrode is driven by an RF signal relative to the channel region, which acts as ground, surrounding the electrode probe. The driving signals on the two electrodes are chosen 180° out of phase to create an alternating electric field between the two electrodes. The RF electric field is modeled and exhibits an electric field intensity which creates a sensing plane across the passageway of the seed sensor. The range of frequencies of operation is between 100 MHz-1.5 GHz.

The RFFP sensors are one port symmetrical networks using a coaxial Fabry-Perot cavity. The RFC sensor is a two port symmetrical network using two capacitive electrodes. The two port network can be converted into a one port network using a reciprocal balun. Thus, both embodiments are effectively one port networks which can be described in terms of a reflection coefficient or one port scattering parameter: S11.

In embodiments, the sensors are non-radiative. Thus, excluding resistive loss and unintentional radiation, the one port driving signal mostly gets reflected back. The phase shift in the reflected signal is a function of the one port S-parameter: S11, which is a function of the presence or the absence of seeds. Thus, when one or more seeds pass through the sensor, the phase of the reflected signal gets changed and is detected, providing better detection capability for small seeds.

An embodiment of a detection scheme for the sensors disclosed above senses the phase modulation of a test signal reflected from the sensor head as it is perturbed by a traversing seed stream. The best sensitivity to phase shift occurs when the sensor head is operated at its resonant frequency. When a seed passes through the sensor it will slightly shift the resonant frequency to the right or left. As a result, if the sensor is operated with a test signal at the nominal resonant frequency, any slight change in the resonance of the sensor due to passing seeds will cause a significant shift in the phase of the reflection coefficient.

Embodiments of basic sensing circuit topologies have been targeted to provide phase detection of a test signal applied to a sensor head tuned to resonance. The first circuit topology includes an RF signal source, a 90 degree coupler, sensor head feed line, and a phase detection circuit. The second circuit topology uses an interferometer technique and includes an RF source, in interferometer network, and an envelope detection circuit. In another embodiment, a phase detector can be used in place of the interferometer network 754.

Environmental conditions could cause the resonant frequency of the sensor to vary or drift. The RF can be dithered to counter resonance drifts. Dithering is a function of the RF circuit that adds some form of phase or frequency modulation to the carrier signal generated by the RF source. This creates a broader band width signal that covers the range of frequencies over which the sensor resonance may vary due to various tolerances. By dithering the exciting RF field in frequency about the nominal resonant frequency, we can ensure that the true resonant frequency is within the bandwidth of the dithered signal. Because the sensitivity is highest at the resonant frequency, the envelope detection will ensure that only the response at the resonance frequency will dominate the detected signal. In another embodiment, a software algorithm could automatically set the output frequency to the sensor resonance based on training from the signal.

In embodiments, the sensor RF signal is demodulated to give an analog signal which is digitized by an analog to digital converter. This digitized signal is communicated to the cab of the tractor through a bus that is standard on current equipment. Thus, the farmer receives real-time feedback during planting operations. Therefore, the embodiments disclosed herein are advantageous in that the seed sensors provide feedback in real-time which allows the farmer to immediately adjust the amount of seed being fed to the seed chute "on-the-fly." Thus, used is the minimum amount of seed resulting in the idealized yield. It further permits the optimum spacing of the seeds.

The low profile and compact design of the disclosed RF/microwave sensors are advantageous because there is generally very little space around the deployment tube of seed planters in which to attach devices. A coaxial waveguide allows propagating modes no matter how constricted the waveguide is. Thus, very compact resonators can be designed by loading a coaxial waveguide with materials of large permittivity.

The RF/microwave sensors of the present invention have been tested and found to count seeds with >99% accuracy and at high seed rates in excess of 100 seeds per second.

Structurally, various embodiments of the invention include an electromagnetic sensor, such as a RF or microwave sensor, comprising a conduit defining a passageway concentric about a central axis and including a first end and a second end, the first end being opposite the second end along the central axis. The conduit can include a first portion proximate the first end and a second portion proximate the second end, with the first portion comprising a first interior portion, the first portion being surrounded by an exterior portion. The first interior portion and the exterior portion define a first annular gap therebetween. The first interior portion and the second portion define a continuous circumferential gap therebetween, the circumferential gap being in fluid communication with the annular gap. A first short connects the first interior portion and the exterior portion of the conduit, the first short and the annular gap defining an electromagnetic cavity. A first electromagnetic probe can be engaged with the first interior portion within the electromagnetic cavity. The electromagnetic cavity and the circumferential gap are configured to establish an electromagnetic field across the conduit and proximate to a plane substantially normal to said central axis. The seed sensor can further comprise an electronic circuit having an electromagnetic signal source output connected to a coupler input, a coupler output connected to a phase detection circuit, and a sensor head feedline bi-directionally connected to the coupler input. The electronic circuit can be adapted to generate the electromagnetic field and detect perturbations in the field.

In some embodiments, the second portion of the conduit is defined by the exterior portion. In other embodiments, the second portion includes a second interior portion that is surrounded by the exterior portion to define a second annular gap therebetween, wherein the second portion is defined by the second interior portion, the second annular gap being in fluid communication with the circumferential gap. In this embodiment, the electromagnetic sensor can further comprise a second short, such that the electromagnetic cavity is further defined by the second annular gap and the second short. A second electromagnetic probe can also be connected to the second interior portion within the electromagnetic cavity.

Various embodiments further comprise an electronic circuit having an electromagnetic source (e.g., an RF synthesizer), an interferometer, and an envelope detector connected to the sensor, the electronic circuit to generate the electromagnetic field and detect perturbations in the field. In one embodiment, the conduit surrounds a seed chute. In certain embodiments, a high permittivity material is disposed within the electromagnetic cavity.

In various embodiments of the invention, there is a electromagnetic sensor including a conduit defining a passageway concentric about a central axis, the conduit including an interior surface, the interior surface having a first side and a second side opposite the first side, the first side defining a first recess and the second side defining a second recess, the first recess and second recess identically configured and facing each other across the passageway. The conduit further defines a first aperture and a second aperture, the first aperture being adjacent and in fluid communication with the first recess and the second aperture being adjacent and in fluid communication with the second recess. A first electrode can be disposed and confined within said first recess and electrically isolated from said conduit. A second electrode can be disposed and confined within said second recess and electrically isolated from said conduit. In one embodiment, a first electromagnetic probe disposed in the first aperture and engaged with the first electrode, said first electrode being configured to be driven by a first electromagnetic signal; likewise, a second electromagnetic probe can be disposed in the second aperture and engaged with the second electrode, the second electrode configured to be driven by a second electromagnetic signal. In one embodiment, the first electromagnetic signal is 180° out of phase with respect to the second electromagnetic signal. An electric field intensity is localized between the first and second electrodes across the passageway and substantially normal to said central axis.

In still other embodiments of the invention, a electromagnetic seed sensor comprises a conduit surrounding a feed chute, an electromagnetic cavity within the conduit, and a sensing field normal to the feed chute. Electronic circuitry can be included to generate an electromagnetic field and detect perturbations in the electromagnetic field. A first driving signal that is 180 degrees out-of-phase with a second driving signal. The perturbations result from one or more seeds crossing the electromagnetic field and are signal phases changes of the transmitted signal or the reflected signal.

Certain embodiments of the invention embody a method of counting seeds passing through a seed chute during agricultural planting operations. The method includes:
  providing a sensor to attach to and surround the seed chute, the sensor creating a sensing plane across a diameter of the seed chute;
  connecting to the sensor an electronic circuit having an electromagnetic source, an interferometer, and an envelope detector;
  introducing an electromagnetic field in the sensor via the electromagnetic source, generating a fringing field penetrating the seed chute and creating a uniform sheet of electromagnetic field in the sensing plane;
  detecting the phase modulation of a signal reflected from the sensor as the electromagnetic field is perturbed by the passing seeds via the interferometer;
  modulating the carrier signal in response to phase variations in the sensor head reflection coefficient;
  providing the modulated carrier to an electromagnetic amplifier gain stage and then to the envelope detector;
  demodulating the carrier signal and providing a base band seed pulse response to an operational amplifier to remove any DC offset and providing further gain; and
  sampling the signal with an analog to digital converter and processing the signal.

BRIEF DESCRIPTION OF THE DRAWINGS

FIG. 6A is a vertical sectional view of a coaxial seed sensor having an extended RF cavity according to an embodiment of the invention.

DETAILED DESCRIPTION

Figure 1:
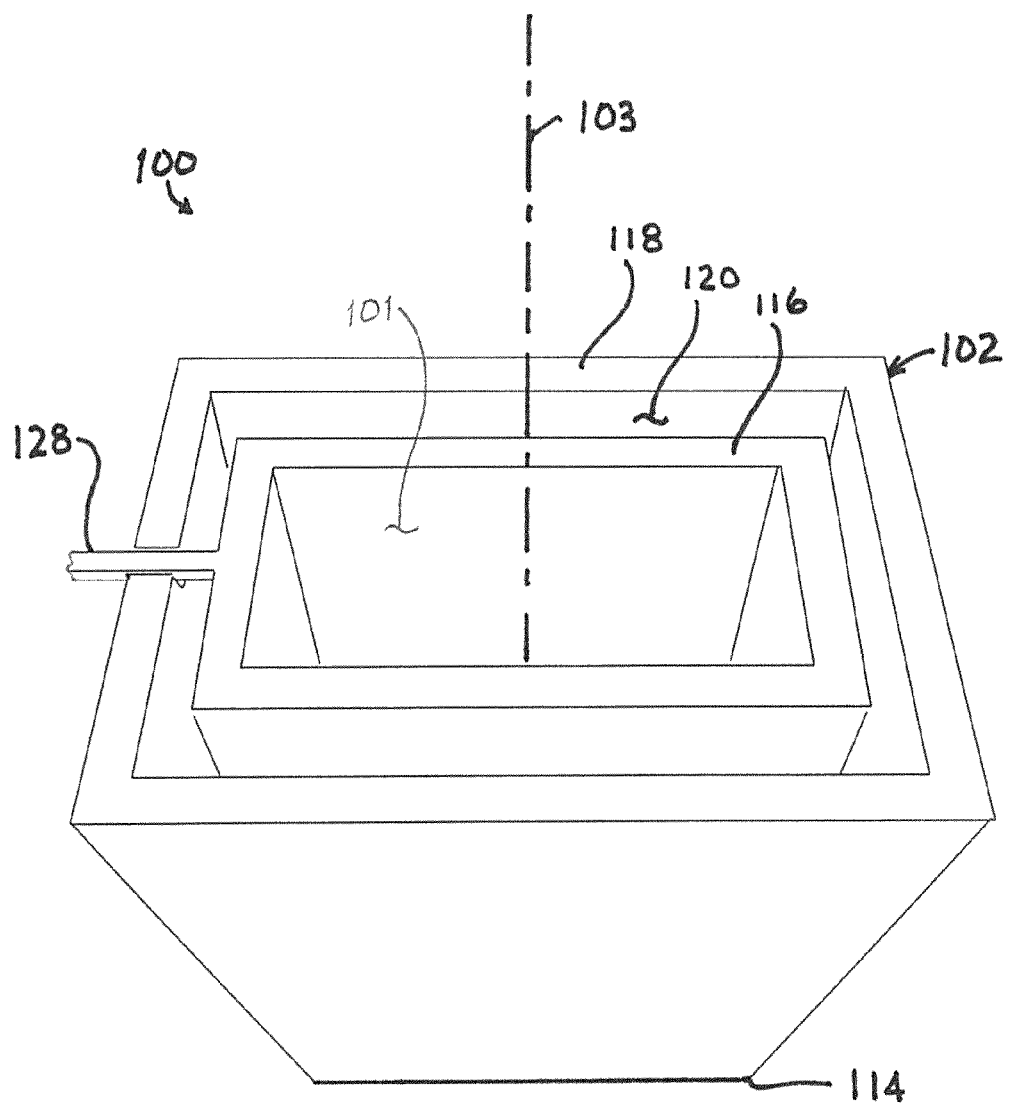
FIG. 1 is a horizontal sectional view of a coaxial seed sensor according to one embodiment of the invention.
Figure 2A:
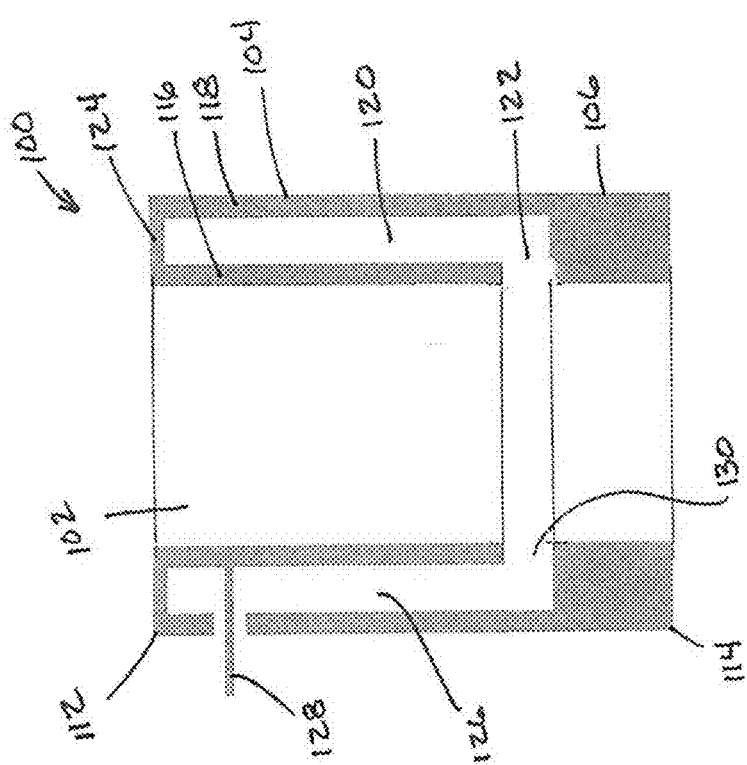
FIG. 2A is a vertical sectional view of a coaxial seed sensor according to an embodiment of the invention.

Referring to FIGS. 1 and 2A, a RF Fabry-Perot (RFFP) sensor 100 is depicted in an embodiment of the invention. The RFFP sensor 100 comprises a conduit 102 defining a passageway 101 concentric about a central axis 103. In one embodiment, the RFFP sensor 100 is configured to resonate as a quarter wavelength resonator at some frequency. The conduit 102 has a first end 112 and an opposing second end 114 disposed along the central axis 103. The conduit 102 further can include a first portion 104 that is proximate the first end 112 and a second portion 106 that is proximate the second end 114. The first portion 104 has an interior portion 116 and an exterior portion 118 in relation to the central axis 103 where the interior portion 116 and exterior portion 118 define an annular gap 120 therebetween. The interior portion 116 and the second portion 106 define a circumferential gap 122 therebetween. The circumferential gap 122 can extend through the thickness of the interior portion 116 so that the annular gap 120 and circumferential gap 122 are in fluid communication.

In one embodiment, a short 124 is disposed at the first end 112 to connect the interior portion 116 and exterior portion 118. The circumferential gap 122 acts approximately as an open. Thus, the RF cavity 126 is formed between the short 124 at one end and open at the other. An RF probe 128 can extend radially through the exterior portion 118 and annular gap 120 to engage the interior portion 116 in the RF cavity 126, the RF probe 128 being electrically isolated from the exterior portion 118. It is understood that the engagement of the RF probe 128 with the interior portion 116 is not limited to the configuration as depicted in the figures. The RF probe 128 can be positioned to engage the interior portion 116 at any location on the interior portion as long as the RF probe 128 is electrically isolated from the exterior portion 118.

Figure 3:
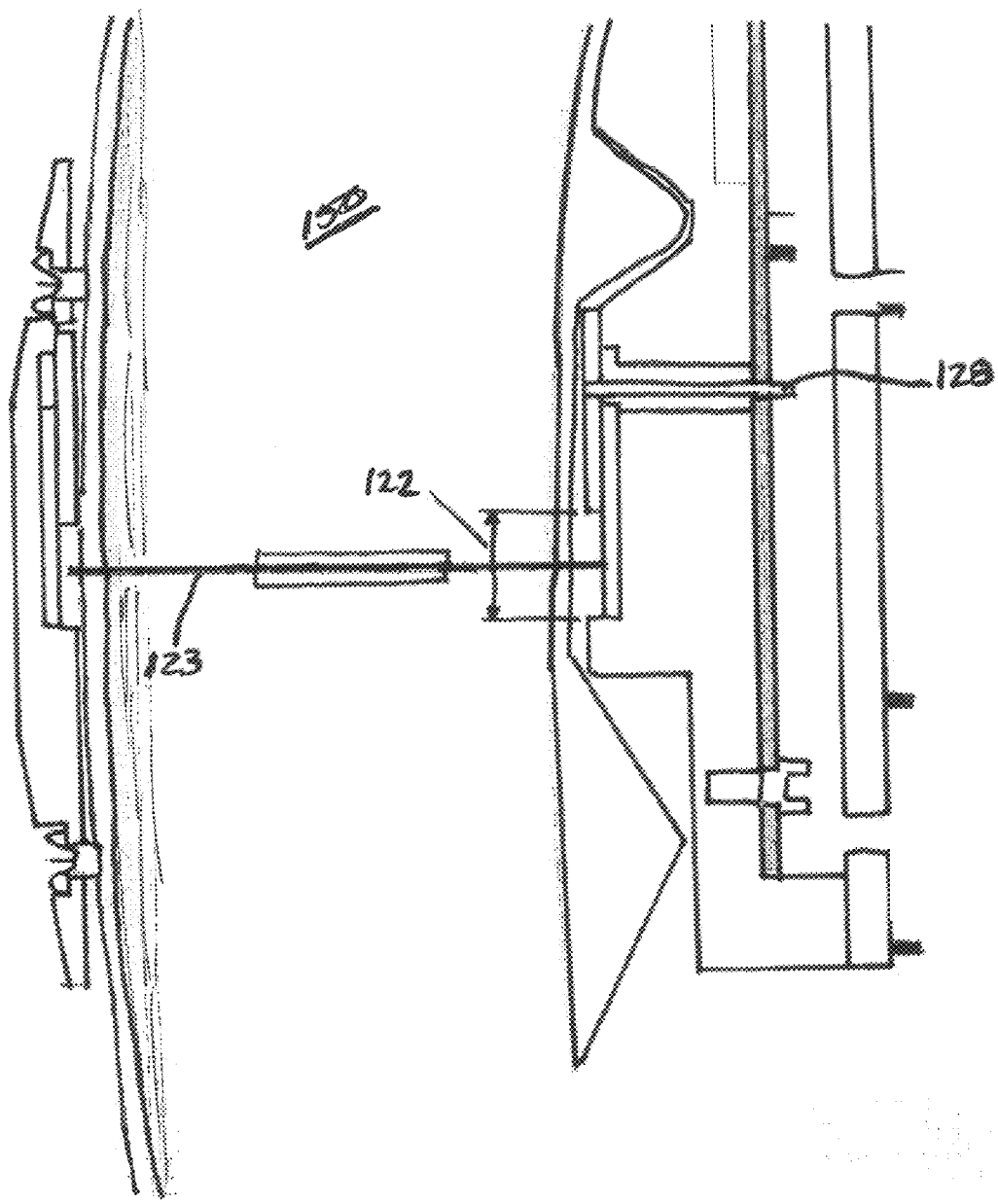
FIG. 3 is vertical sectional view of a coaxial seed sensor that surrounds a seed tube illustrating the sensing plane in an embodiment of the invention.

In the embodiment shown in FIG. 1, the conduit 102 is depicted as being substantially rectangular. However, it is apparent to those skilled in the art that the conduit 102 can be any shape that complements the seed tube 150 (FIG. 3). The conduit 102 can be made of a metal that has good conductivity or of a plastic coated with a good conductivity metal, e.g., aluminum, zinc, tin, copper, magnesium and their alloys or steel and variants of steel which are machinable, highly conductive, die castable materials that can be coated with a conductive and environmentally protective coating.

Figure 2B:
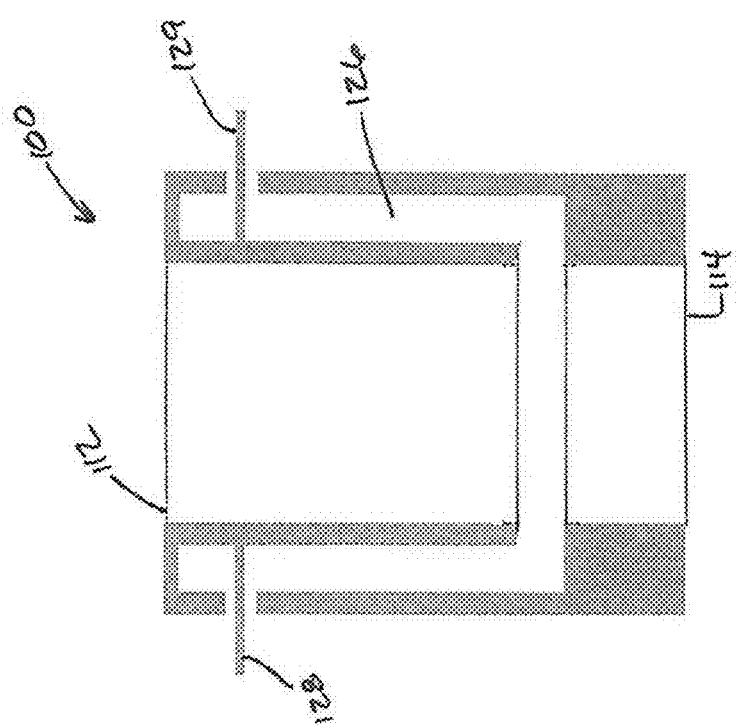
FIG. 2B is a vertical sectional view of a coaxial seed sensor having two probes according to an embodiment of the invention.

FIG. 2B depicts an embodiment of a sensor 100 having a second probe 129 disposed in the RF cavity 126. In the embodiments shown in FIGS. 2A and 2B, probes 128, 129 are used near the shorted end of the RF cavity 126. However, it is to be understood that the probes 128, 129 locations are not so limited and they can be provided to engage with any point on the interior portion 116 as long as they are electrically isolated from the exterior portion 118. In an embodiment, two probes 128, 129 provide a transmission setup where the first probe is excited by an RF field and the transmitted RF field at the second probe is monitored.

FIG. 3 illustrates the circumferential gap 122 and the sensing region 123. Example and non-limiting dimensions for the circumferential gap 122 can range from about 0.1 cm to about 2.0 cm. These dimensions were chosen to maximize the field uniformity and the extent of the sensing plane 136 (FIG. 4A) along the seed tube 150. Example and non-limiting dimensions for the annular gap 120 can range from about 0.05 cm to about 1.0 cm.

In operation, excitation of the RF cavity 126, via the RF probe 128, results in a fringing field that penetrates the passageway 101 from all sides thus creating a sensing plane 123 where the electric field intensity is large. The RFFP sensor 100 can be a quarter wavelength or half wavelength coaxial-resonator cavity. It is understood that the wavelengths are quarter wavelengths incrementally increased by half wavelengths, e.g., 1/4, 3/4, 5/4, etc. and half wavelengths incrementally increased by half wavelengths, e.g. 1/2, 2/2, 3/2, 4/2, 5/2, etc. Half wavelength coaxial-resonator cavities are described in relation to FIG. 5 and resonator is shorted at both ends 112, 114. The fringing field from the cavity penetrates the sensing region and generates a uniform sheet of RF near field within the seed tube 150. Thus, this embodiment has a resonant cavity. However, unlike RF sensors of the prior art, the seeds do not pass through the resonant cavity. The resonant aspect of the RFFP sensor 100 allows for good seed detectability. In one embodiment, the sensor operates at a frequency of approximately 2.5 GHz to approximately 3.0 GHz. In another embodiment, the sensor operates at a frequency of approximately 200 MHz to approximately 6.0 GHz.

In an embodiment, the RFFP sensor 100 can operate at a frequency different from the resonance frequency. Any loss in seed sensitivity can be compensated for by increasing the amplification in the electronic circuit.

Figure 4A:
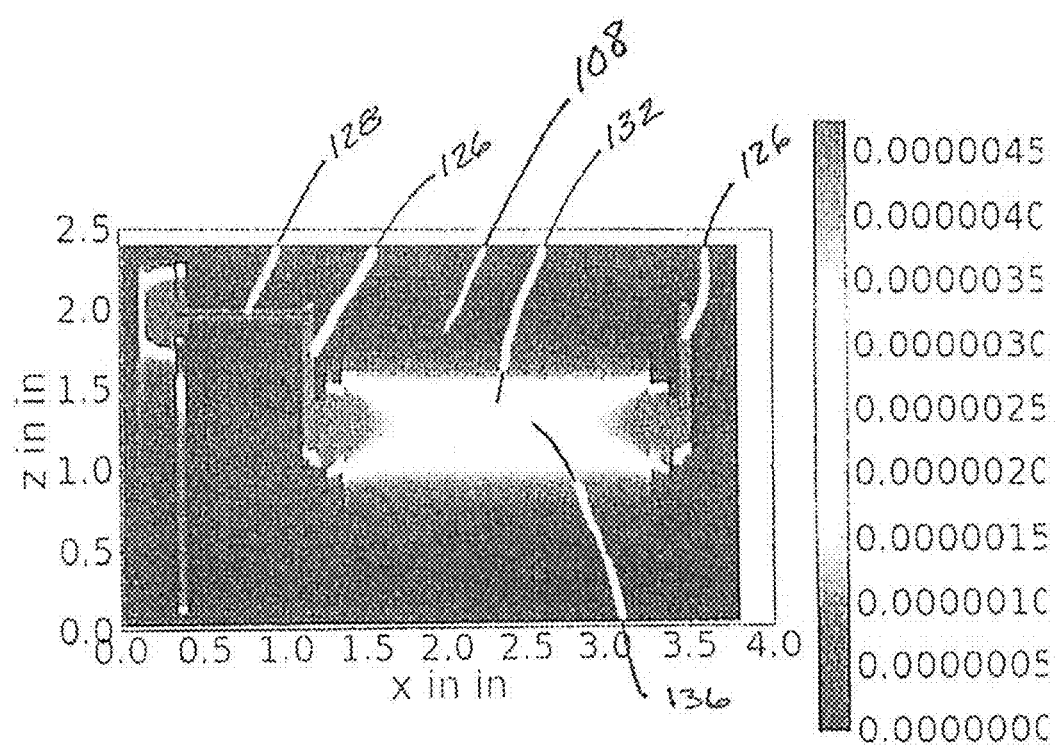
FIG. 4A depicts electric field intensity having an arbitrary linear scale in a sensing plane in an embodiment of the invention.

Referring to FIG. 4A, a modeled electric field intensity 132 in the sensing plane 136 for the RFFP sensor 100 in an embodiment of the invention. The electric field intensity 132 is preferably localized so that the sensing field is substantially uniform and "constricted," i.e., substantially within a limited dimension in the direction of the central axis 103. The geometry of the depicted electric field intensity 132 is generally rectangular, but is not so limited.

The mode excited in the seed tube 150 is a non-radiating mode. Nonetheless, any loss of symmetry in the structure could excite parasitic modes that could radiate. The interior portion 116 and the region 106 form cut off waveguides that cut off any such radiation. Cut off waveguides on both sides of the sensing plane 136 forces confinement and prevents radiation of the electric field.

Figure 4B:
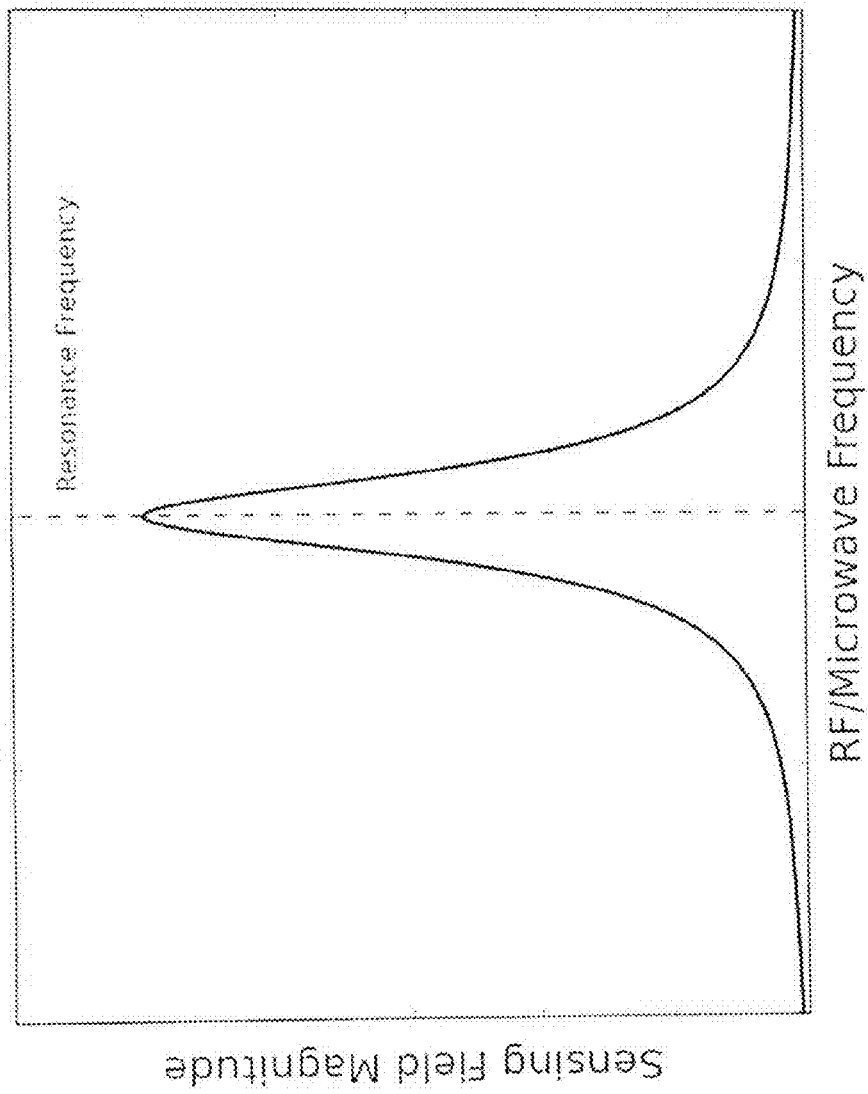
FIG. 4B depicts a modeled resonance frequency for a resonator in an embodiment of the invention.

Functionally, the RFFP sensor 100 forms a coaxial Fabry-Perot cavity. The RF cavity 126 effectively forms a transmission line analogous to a coaxial cable. Due to the short 124 at the first end 112 and the open 130 at the circumferential gap 122, the line can resonate as a quarter wavelength resonator at some frequency. FIG. 4B depicts a modeled resonance frequency for a resonator. In practice, the open 130 is not a perfect open and can have parasitic reactance. FIG. 2A shows the RF cavity 126 shorted at the first end 112 and opened towards the passageway 101. The open 130 creates a fringing field that penetrates the seed tube 150 from all sides. This creates the sensing plane 136 where the electric field intensity 132 is large. The RF cavity 126 can be excited using standard cavity excitation techniques. In the embodiment shown, a probe 128 is used near the shorted end of the RF cavity 126. However, it is to be understood that the probe 128 location is not so limited and it can be provided to engage with any point on the interior portion 116 as long as it is electrically isolated from the exterior portion 118.

Figure 5:
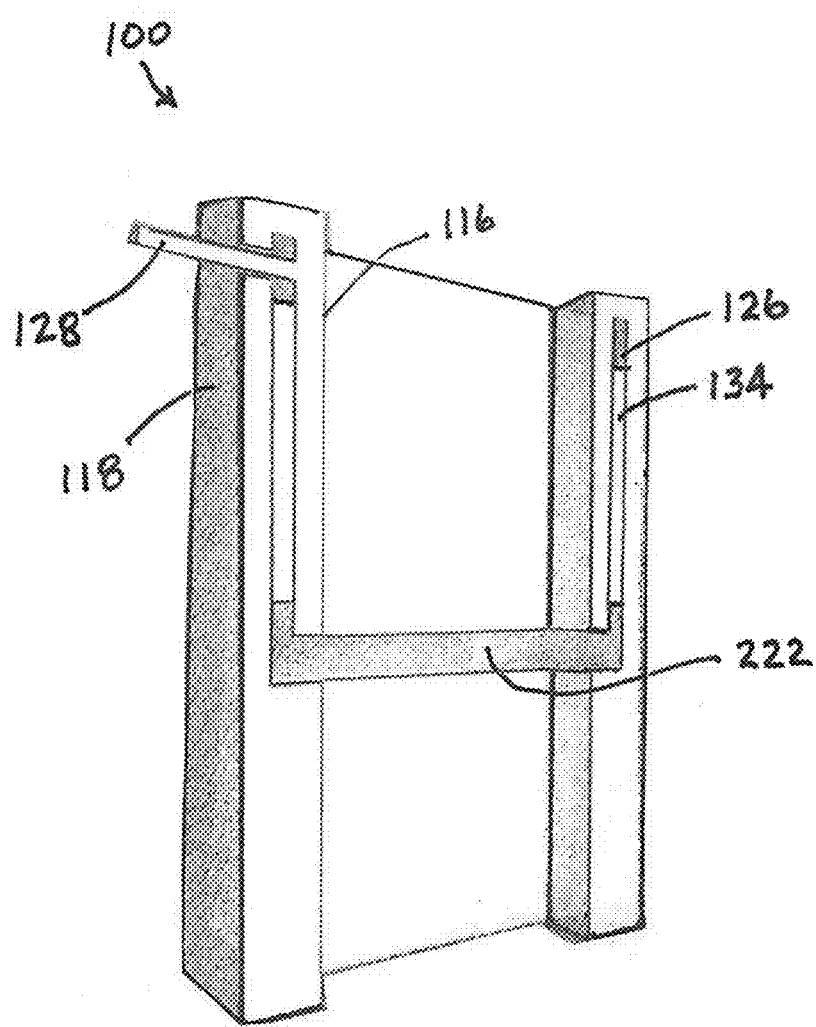
FIG. 5 is a vertical sectional view of a coaxial seed sensor having material with large permittivity in the RF cavity according to an embodiment of the invention.

Referring to FIG. 5, the resonant cavity 126 is depicted as partially filled with a high permittivity material 134 having a large dielectric constant. Whether a sensor 100 is resonant depends on the frequency of operation. The RFFP sensor 100 can be operated in a self-resonant mode. The range of frequencies of operation for this design is about 200 MHz to about 6.0 GHz. There could be practical constraints that could prevent the sensor 100 from being long enough to form a resonator. In this case, the length of the resonant cavity 126 can be shortened by loading the cavity with the high K material 134, e.g., Delrin® acetal resin, resins/elastomers impregnated with high permittivity ceramics. The relative permittivity for such a loading material can be in the range of about 2 to about 100.

Figure 6B:
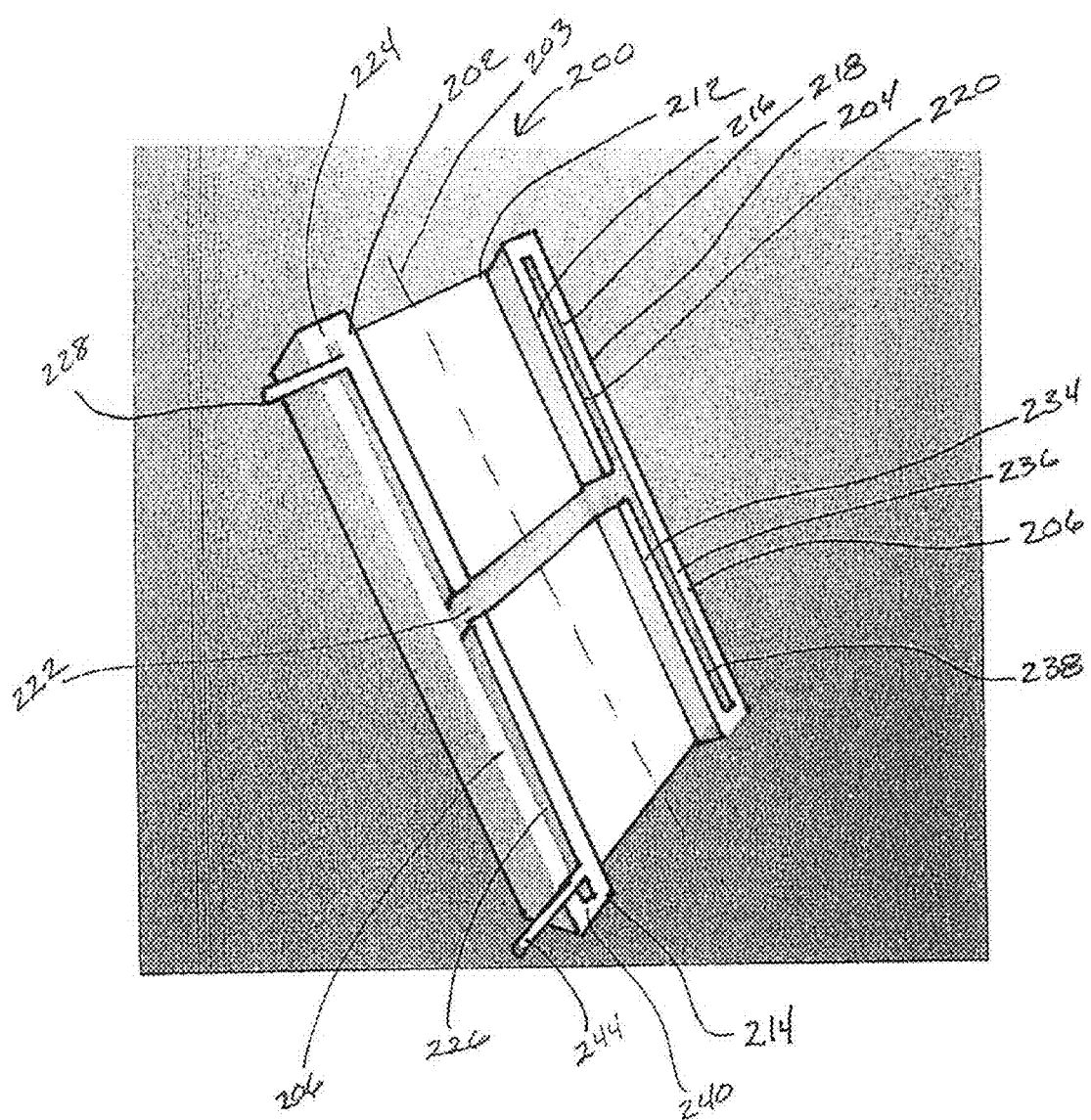
FIG. 6B is a vertical sectional view of a coaxial seed sensor having an extended RF cavity and two probes according to an embodiment of the invention.

Referring to FIG. 6A, a half wavelength RFFP resonator 200 is depicted in an embodiment of the invention. In addition to the RF cavity 226, the half wavelength RFFP 100 includes an RF cavity 227 in the second portion 206 and shorting both ends of the RFFP resonator 200. A conduit 202 defining a passageway 201 has a first end 212 and an opposing second end 214 disposed along the central axis 203.

The conduit 202 further can include a first portion 204 that is proximate the first end 212 and a second portion 206 that is proximate the second end 214. The first portion 204 has an interior portion 216 and an exterior portion 218 in relation to the central axis where the interior portion 216 and exterior portion 218 define an annular gap 220 therebetween. The second portion 206 has an interior portion 234 and an exterior portion 236 in relation to the central axis where the interior portion 234 and exterior portion 236 define an annular gap 238 therebetween. The interior portion 216 and the interior portion 234 define a circumferential gap 222 therebetween. The circumferential gap 222 can extend through the thickness of the interior portions 216, 234 so that annular gaps 220, 238 and circumferential gap 222 are in fluid communication.

In one embodiment, a short 224 is disposed at the first end 212 to connect the interior portion 216 and exterior portion 218. Another short 240 is disposed at the second end 214 to connect the interior portion 234 and exterior portion 236. In providing the shorts 224, 240, an RF cavity 226, 242 is created in the annular gap 220, 238. In one embodiment, the cavity 226, 242 can be excited using one probe 228 providing a reflection setup and the reflected field is monitored at the probe 228. In another embodiment, shown in FIG. 6B, the cavity 226, 242 can be excited using two probes 228, 244. A first RF probe 228 is provided to engage with the interior portion 216 in the RF cavity 226. A second RF probe 244 is provided to engage with the interior portion 234 in the RF cavity 244. The RF probes 228, 244 are electrically isolated from the exterior portion 218, 236. Both probes 228 and 244 can be excited in phase and the reflection monitored. In an embodiment, two probes 228, 244 provide a transmission setup where the first probe is excited by an RF field and the transmitted RF field at the second probe is monitored.

Figure 6C:
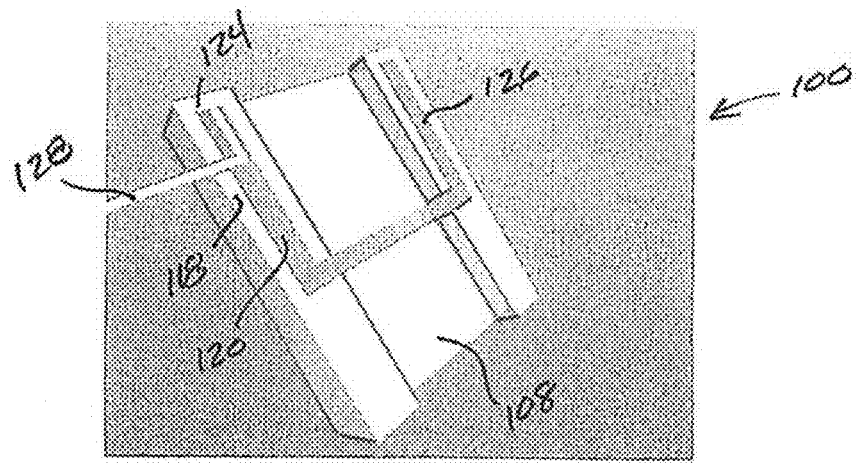
FIG. 6C is a vertical sectional view of the sensor with the probe converted into a loop and engaged with the short.
Figure 6D:
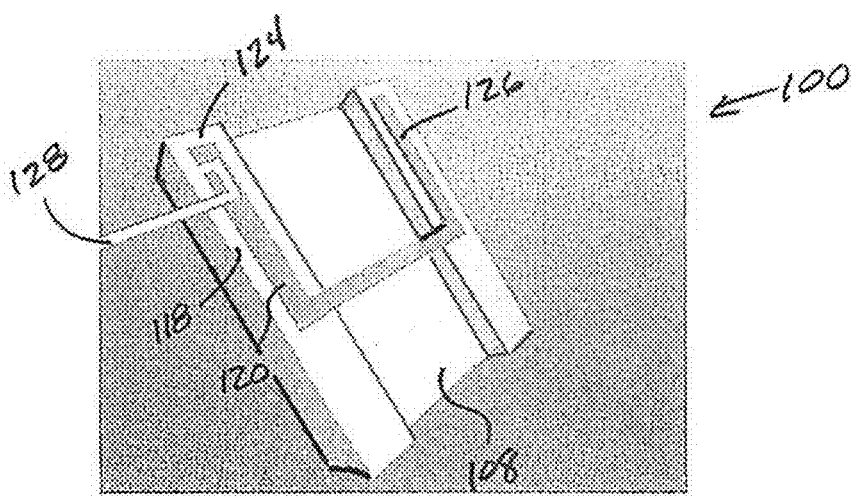
FIG. 6D is a vertical sectional view of the sensor with the probe converted into a loop and engaged with the exterior portion.

Referring now to FIGS. 6C and 6D, there are shown two example embodiments of alternative designs to the feed line of devices shown in FIGS. 1 to 6B. In particular, the probe instead of being engaged with the interior portion is instead converted into a loop and engages with the short (FIG. 6C) or the exterior portion (FIG. 6D). And, while shown in the embodiment of the RF sensor 100, one with skill in the art understands that this embodiment is equally applicable to RF sensors 200, 600. In other embodiments, not shown, it is understood that more than one probe can be provided in the embodiments of FIGS. 6C and 6D.

In the embodiments shown in FIGS. 5, 6 and 6A, the conduit 202 is depicted as being substantially rectangular. However, it is apparent to those skilled in the art that the conduit 202 can be any shape that complements the seed tube 150. The conduit 202 can be made of a metal that has good conductivity or of a plastic coated with a good conductivity metal, e.g., aluminum, zinc, tin, copper, magnesium and their alloys or steel and variants of steel which are machinable, highly conductive, die castable materials that can be coated with a conductive and environmentally protective coating.

Example and non-limiting dimensions for the circumferential gap 222 can range from about 0.1 cm to about 2.0 cm. These dimensions were chosen to maximize the field uniformity and bandwidth of the sensing plane. Example and non-limiting dimensions for the annular gap 220, 238 can range from about 0.05 cm to about 1.0 cm.

Excitation of the cavity 226, 242, via the RF probe 228, 244 results in a fringing field that penetrates the passageway 201 from all sides thus creating a sensing plane where the electric field intensity is large.

For the RFFP sensors 100 and 200, the coupling can be improved which determines the amount of energy transferred into the resonator 100, 200. In order to change the coupling, the various RF probes 128, 228, 244 can be moved further from or closer to the ends 112, 114, 212, 214. Another way to change the coupling is to provide a high permittivity dielectric material, such as Delrin® or a ceramic impregnated resin, between the RF probe 128, 228, 244 and the shorts 124, 224, 240. In another embodiment, the high permittivity dielectric material, can contact the RF probe 128, 228, 244.

Figure 7A:
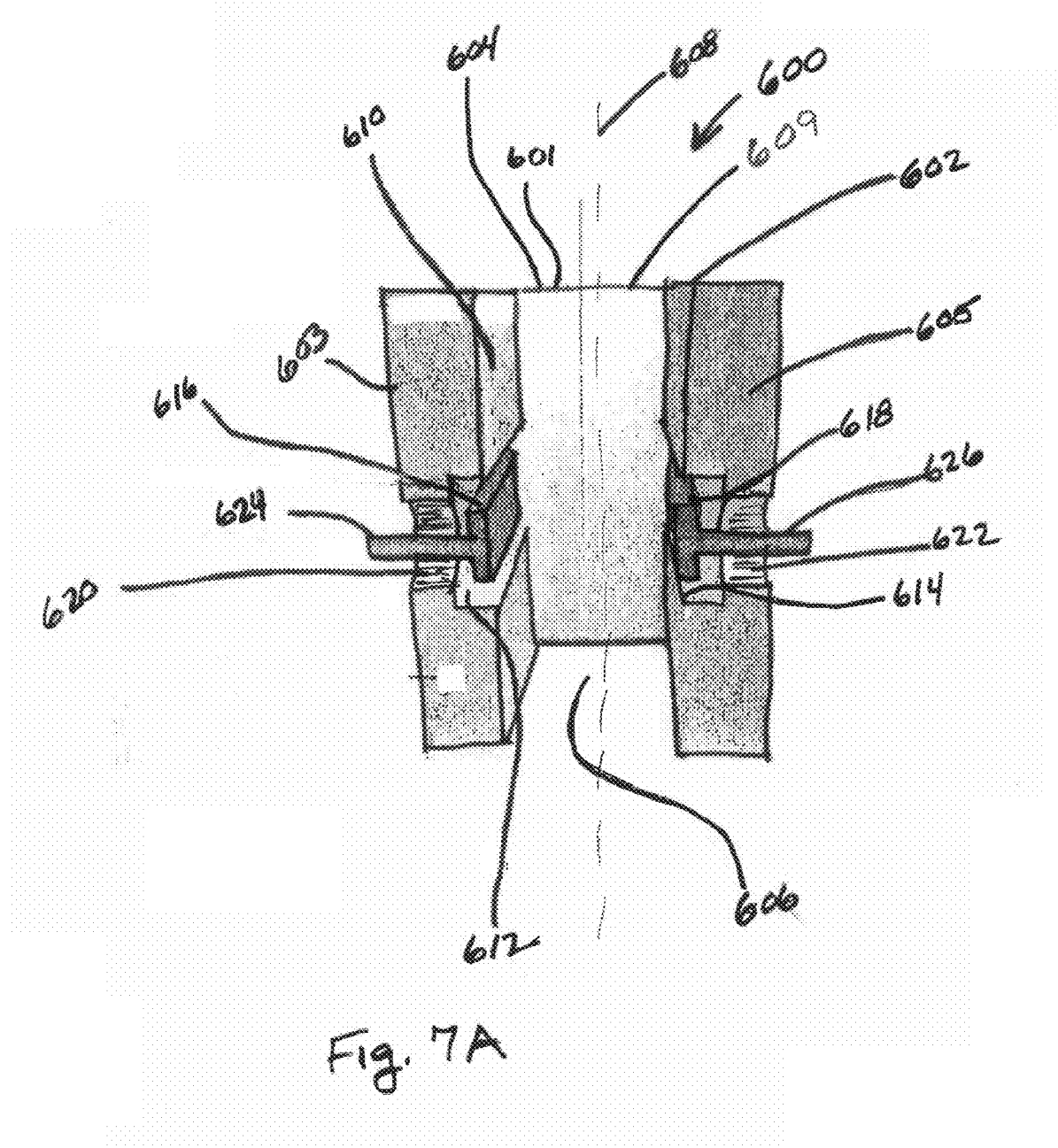
FIG. 7A is a vertical sectional view of a capacitive seed sensor according to an embodiment of the invention.
Figure 7B:
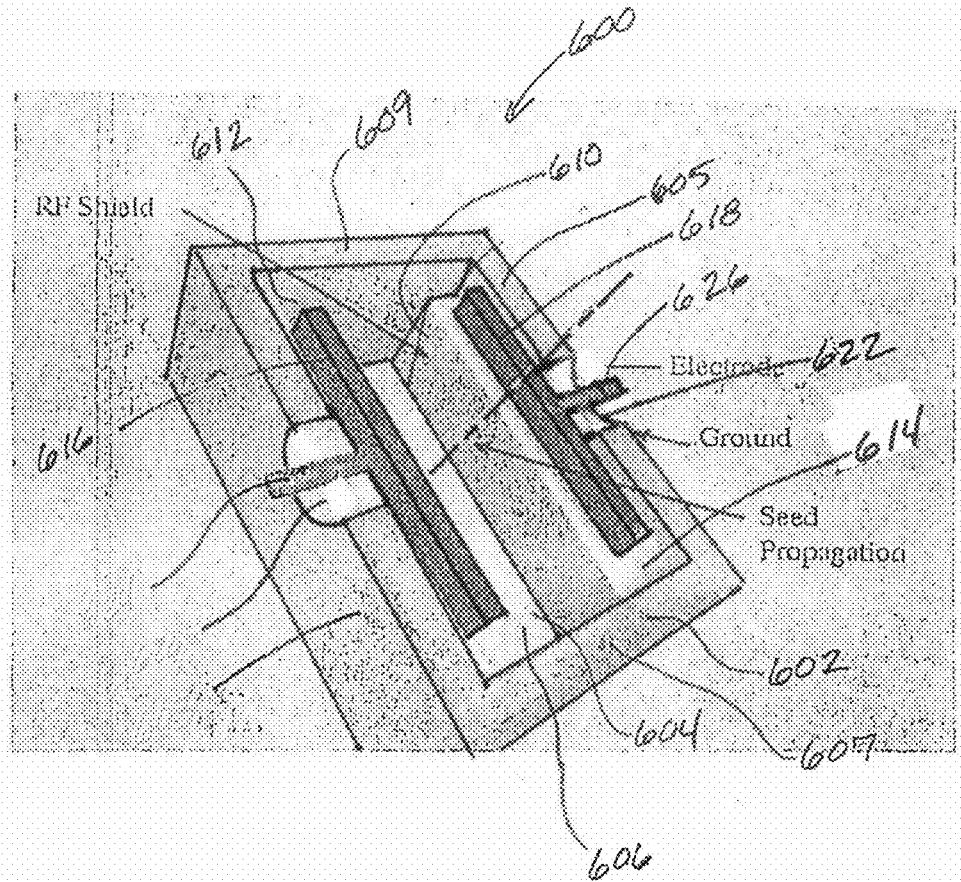
FIG. 7B is a horizontal sectional view of a capacitive seed sensor according to an embodiment of the invention.
Figure 9:
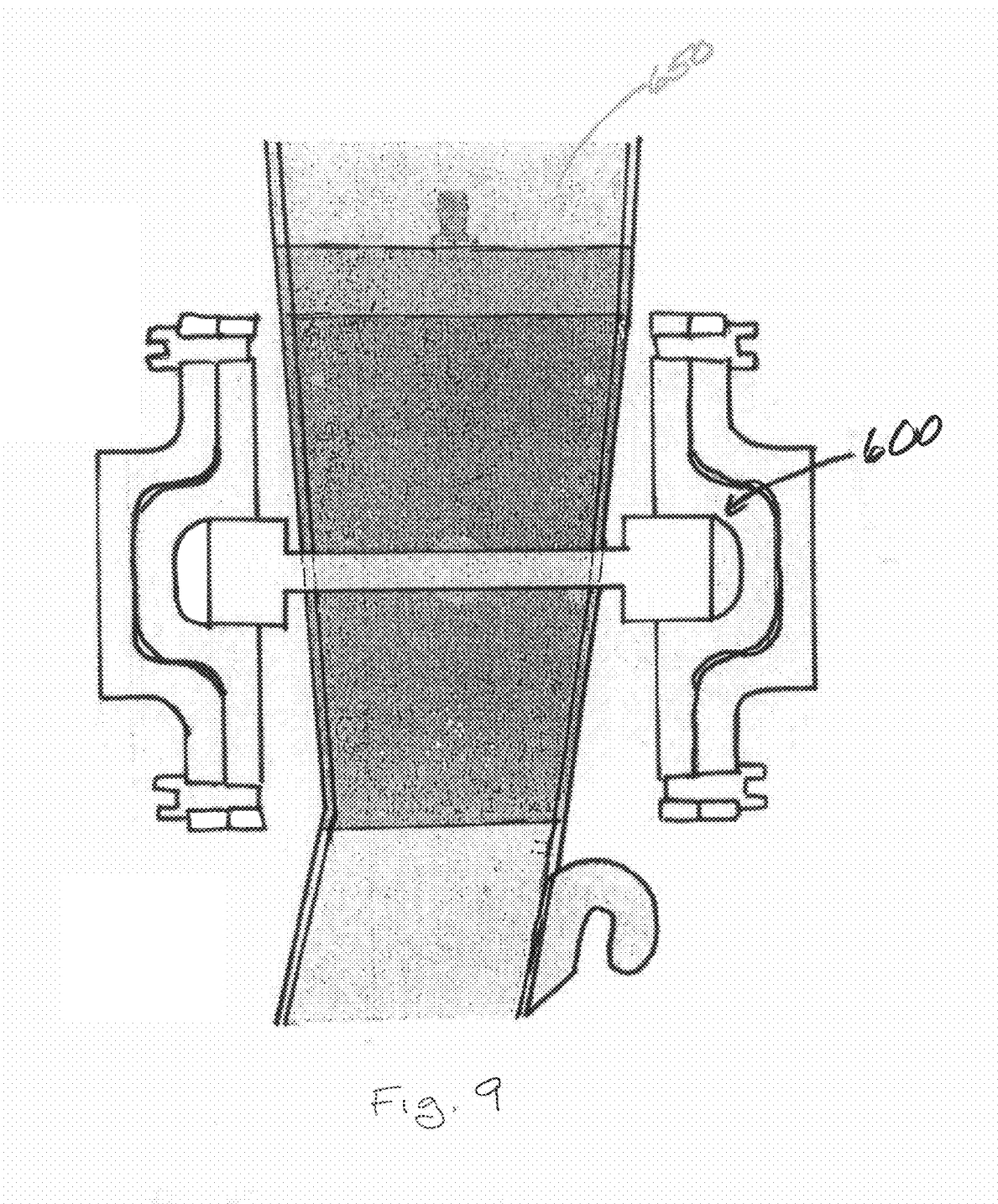
FIG. 9 is a sectional view of a capacitive seed sensor in an embodiment of the invention.

Referring to FIGS. 7A and 7B, a RF capacitive (RFC) sensor 600 is depicted in an embodiment of the invention. The RFC sensor 600 surrounds the seed tube 650 and uses two electrodes that are located on opposite sides of the seed tube 650 (FIG. 9). The RFC sensor 600 includes a conduit 602 defining a passageway 601. The conduit 602 comprises a cavity 606 through which the seeds travel. The conduit 602 is concentric about a central axis 608. The conduit 602 has an interior surface 610, generally with a first side wall 603, a second side wall 605, a front wall 607, and a back wall 609.

The side walls 603, 605 define a first recess 612 and a second recess 614 normal to the central axis 608. The recesses 612, 614 are identically configured and in alignment with each other. The recesses 612, 614 span the side walls 603, 605 so that they abut the front wall 607 on a first end and the back wall 609 on a second end. The recesses 612, 614 are sized to accept a respective first electrode 616 and second electrode 618. The electrodes 616, 618 are electrically isolated from the conduit 602, and can be held in place using non-conducting inserts (not depicted). The conduit 602 defines a first aperture 620 and a second aperture 622 that are adjacent to the first recess 612 and the second recess 614. The aperture 620, 622 and recess 612, 614 thus are in fluid communication with each other. A first RF probe 624 is provided in the first aperture 620 and engages with the first electrode 616 and a second RF probe 626 is provided in the second aperture 622 and engages with the second electrode 618. Each electrode 616, 618 is driven by an RF signal relative to a channel region, defined by the apertures 620, 622, surrounding the probe 624, 626.

As depicted in FIGS. 7A and 7B, the channel 602 is substantially rectangular. However, it is apparent to those skilled in the art that the channel 602 can be any shape that complements the seed tube 650 as long as the electrodes 616, 618 are on opposite side of the seed tube 650 and aligned. The conduit 602 can be made of a metal that has high electrical conductivity or of a plastic coated with a high electrical conductivity metal, e.g., aluminum, zinc, tin, copper, magnesium and their alloys or steel and variants of steel which are machinable, highly conductive, die castable materials that can be coated with a conductive and environmentally protective coating.

In operation, the RF signal on the first electrode 616 is 180° out-of-phase with the RF signal on the second electrode 618. The 180° phase difference ensures that the electric field between the electrodes is in the same direction across the sensing plane and is directed from one electrode to the other. The electric field intensity 628 is localized between the electrodes 616, 618 across the passageway 601 and substantially normal to said central axis 608.

Figure 8:
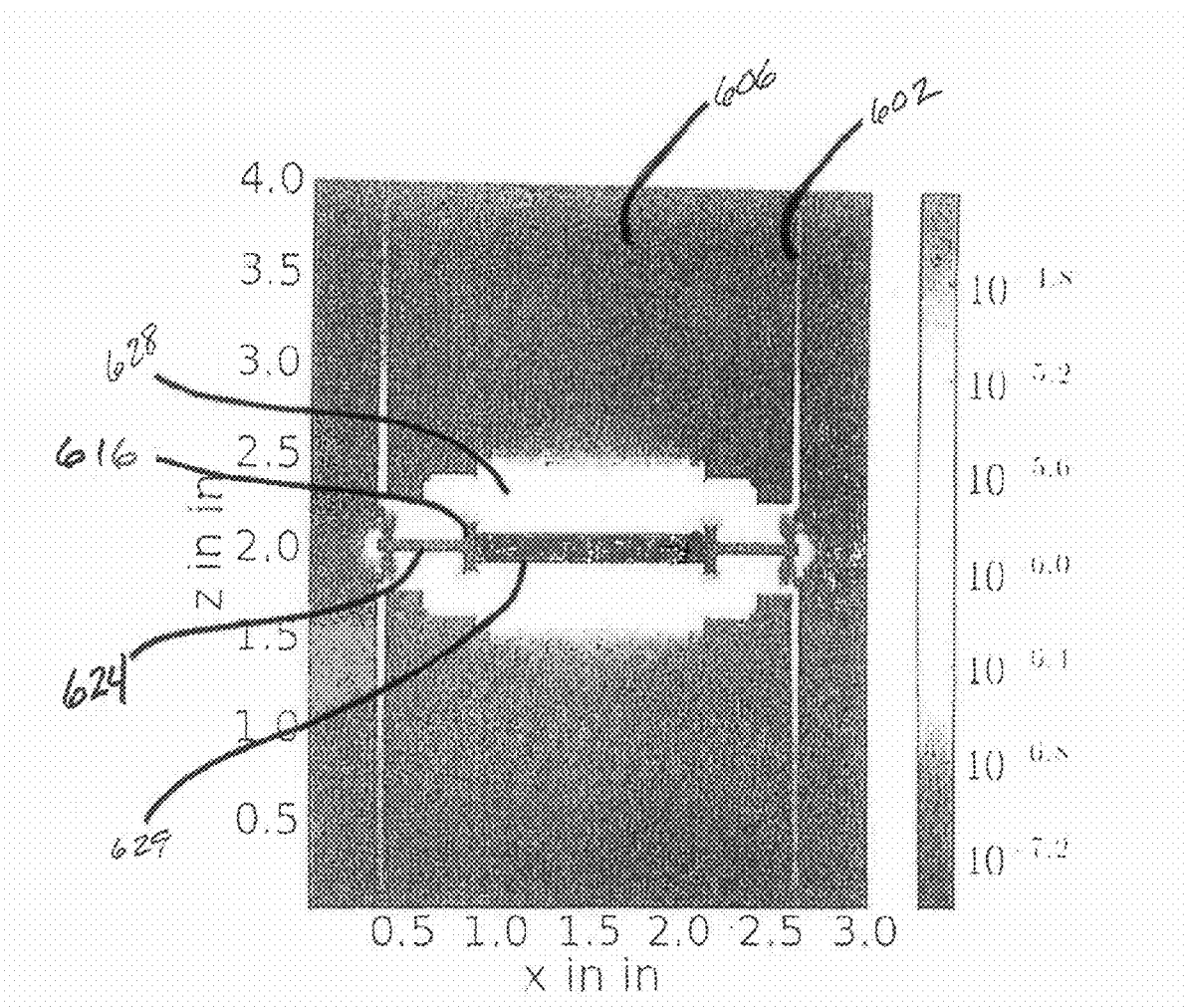
FIG. 8 depicts a capacitive seed sensor electric field intensity having an arbitrary decade scale between the two electrodes in the sensing plane in an embodiment of the invention.

Referring to FIG. 8, the electric field generates a substantially uniform sheet of RF near field 628 within the seed tube. The modeled electric field intensity 628 creates a sensing plane 629. The electric field intensity 628 is preferably localized so that the sensing field is substantially uniform and constricted. The electric field intensity 628 provides full planar coverage of the passageway 601 so that any seed passing through the plane will be detected. The geometry of the electric field intensity 628 is generally rectangular, but is not so limited.

A strong oscillating electric field generated between the electrodes will radiate. The interior portion 610 forms a cut off waveguide that cuts off any such radiation. Cut off waveguides on both sides of the sensing plane forces confinement and prevents radiation. In the absence of this shielding region, the mode excited between the electrodes can radiate through the seed tube 650.

Functionally, unlike previous capacitive designs, the driving voltage is not directly applied between the two electrodes 616, 618. Each electrode is excited by a separate RF signal. Further, there have been subsequent non-resonant designs, however, these designs neither use a phase differential excitation nor use phase detection. Each electrode 616, 618 is instead driven by an RF signal relative to the channel region surrounding the electrode probe 624, 626. This neighboring channel region acts as the ground. The driving signals on the two electrodes 616, 618 are chosen 180° out of phase. This creates an alternating electric field between the two electrodes 624, 626. Using a developed high frequency field modeler tool, the RF electric field is modeled and exhibits an electric field intensity 628 as shown in FIG. 8. The localization of the electric field intensity 628 between the electrodes 616, 618 can be seen. This electric field 628 creates a sensing plane 629 across the passageway 601 of the seed sensor 600. When the seed crosses the sensing plane 629, it gets detected. The range of frequencies of operation is between 100 MHz-1.5 GHz. In this frequency range, the sensor 600 is not self-resonant. The sensitivity of the sensor 600 can be improved by using the sensor 600 in a resonance circuit with external tuning elements such as inductors, capacitors, and resistors.

The RFFP sensors 100 and 200 are one port symmetrical networks using a coaxial Fabry-Perot cavity. The RFC sensor 600 is a two port symmetrical network using two capacitive electrodes. The two port network can be converted into a one port network using a reciprocal balun that takes in a one port signal and converts it into a two port signal with the signals at the two ports being 180° out of phase. Reciprocally, the scattered signals from the two ports get combined 180° out of phase into a one port scattered signal. Thus, both embodiments are effectively one port networks which can be described in terms of a reflection coefficient or one port scattering parameter: S11.

In embodiments, the sensors are non-radiative. Thus, excluding resistive loss and unintentional radiation, the one port driving signal mostly gets reflected back. The phase shift in the reflected signal is a function of the one port S-parameter: S11, which is a function of the presence or the absence of seeds. Thus, when one or more seeds pass through the sensor, the phase of the reflected signal gets changed and is detected, thus detecting the seed. The seed also has some loss. This will also cause a small change in the amplitude of the reflected signal. However, the loss factor of a seed is small. Thus, detecting the phase shift provides better detection capability for small seeds.

In the presence of an electromagnetic field (that is fairly uniform across the seed), electrical dipoles are induced in the seed and this dipolar response gets detected. The electromagnetic field driving the sensor creates an electric field at the seed location. Reciprocally, the dipole induced in the seed creates an additional field at the driven location. Thus, if the seed is located at a location where the sensor does not create an electric field, the seed will not be detected. Hence, the uniformity of the seed signal depends on the uniformity of the sensor field while the bandwidth of the seed signal depends on the extent of the sensor field. Therefore, to get a large bandwidth and ensure the seed is detected the sensor electric field needs to be tightly localized.

The phase change from a seed is small. Moreover, the phase change from multiple seeds is additive (Main response from a seed is dipolar. The dipole moments from the seeds add up. If we neglect the dipole-dipole interaction, the signal is effectively coming from a single dipole moment qual to the sum of the dipole moments). If the seeds are uniform, the sensitivity of the sensor is uniform across the seed tube cross-section, and if the seeds fall with the same velocity, the area under all phase pulses should roughly be the same. Moreover, they should be additive. Thus, by monitoring the area under the phase signal, it should be possible to count the number of seeds. If there is variability in the seed pulse areas, the variability should average out over any interval discernible to the farmer. This concept forms part of the seed counting algorithm disclosed herein.

Figure 10:
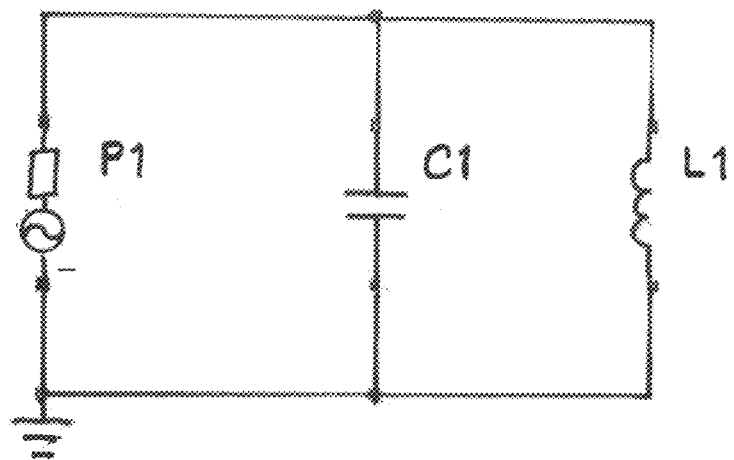
FIG. 10 depicts a resonant circuit.
Figure 11:
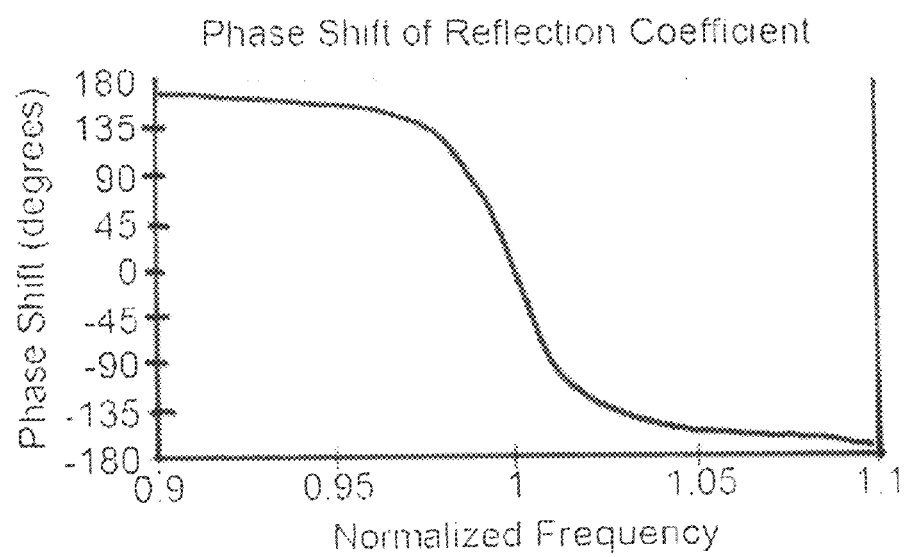
FIG. 11 depicts the phase shift of the resonant circuit of FIG. 10.

An embodiment of a detection scheme for the sensors 100, 200, 600 disclosed above senses the phase modulation of a test signal reflected from the sensor head as it is perturbed by a traversing seed stream. The best sensitivity to phase shift occurs when the sensor head is operated at its resonant frequency. FIG. 10 illustrates, as a simple example, an LC resonant circuit and, in FIG. 11, the phase of its reflection coefficient about the resonant frequency. The phase shift decreases monotonically with frequency and is steepest at the resonant frequency. The sensor heads of the above RF seed sensor designs are tunable to provide a resonant response similar to the case shown in FIG. 11, such that when a seed passes through the sensor it will slightly shift the resonant frequency to the right or left. As a result, if the sensor is operated with a test signal at the nominal resonant frequency, any slight change in the resonance of the sensor due to passing seeds will cause a significant shift in the phase of the reflection coefficient.

As has been described, when a seed passes through the sensor, a seed pulse is generated. In embodiments where multiple seeds are dropped, a pulse sharpening filter that narrows the pulse can be used in the circuit.

The sensor couples to the external circuit through a single port. The reflection or complex phasor at this single port system is monitored for the seed signal. In testing, two embodiments of basic sensing circuit topologies have been targeted to provide phase detection of a test signal applied to a sensor head tuned to resonance.

Figure 12:
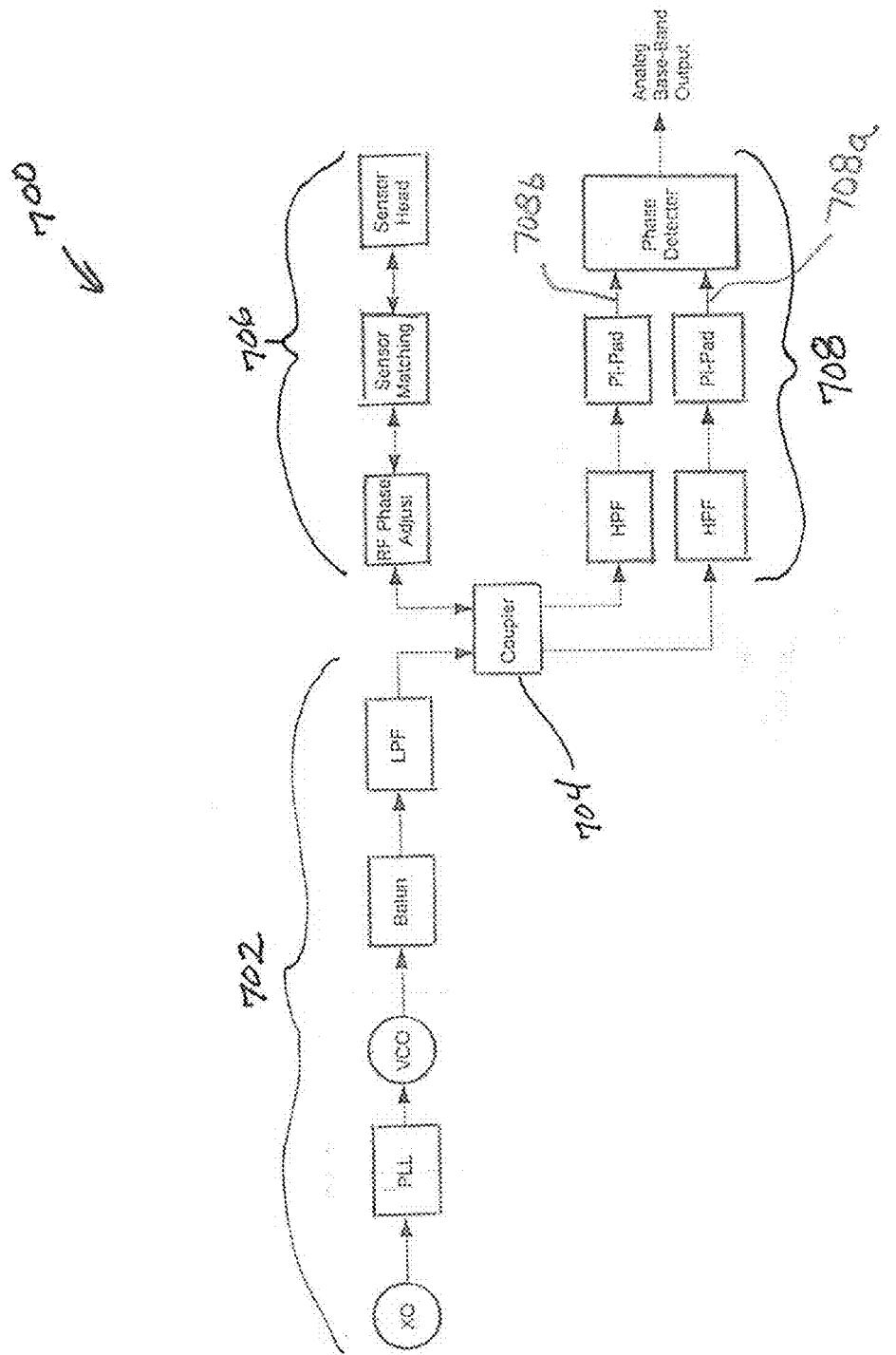
FIG. 12 depicts a sensing circuit topology that provides phase detection of a test signal applied to a sensor head tuned to resonance according to an embodiment of the invention.

The first circuit topology 700 embodiment, as depicted in FIG. 12, includes an RF signal source 702, a 90 degree coupler 704, sensor head feed line 706, and a phase detection circuit 708. The phase detector includes a reference input 708a and a sensing input 708b. The sensing input 708b senses the reflected signal from the sensor head. The 90 degree coupler 704 splits the carrier signal generated by the RF signal source 702 between two paths, one leading to the sensor head feed line 706, and the other to the reference input 708a of the phase detection circuit 708. The carrier signal going to the sensor head feed line 706 will be reflected back to the coupler 704 and will contain PM modulation in response to phase variations in the sensor head reflection coefficient resulting from seeds passing through the sensor. The coupler 704 provides a portion of the reflected carrier signal to the sensing input 708b of the phase detection circuit 708. There are various ways to implement a phase detection circuit 708 one such implementation utilizing an integrated component consisting of limiter amplifiers feeding a high speed phase comparator. The phase detection circuit 708 compares the phase difference between the reference and sensing inputs and produces a PM demodulated base band seed pulse response.

Figure 13:
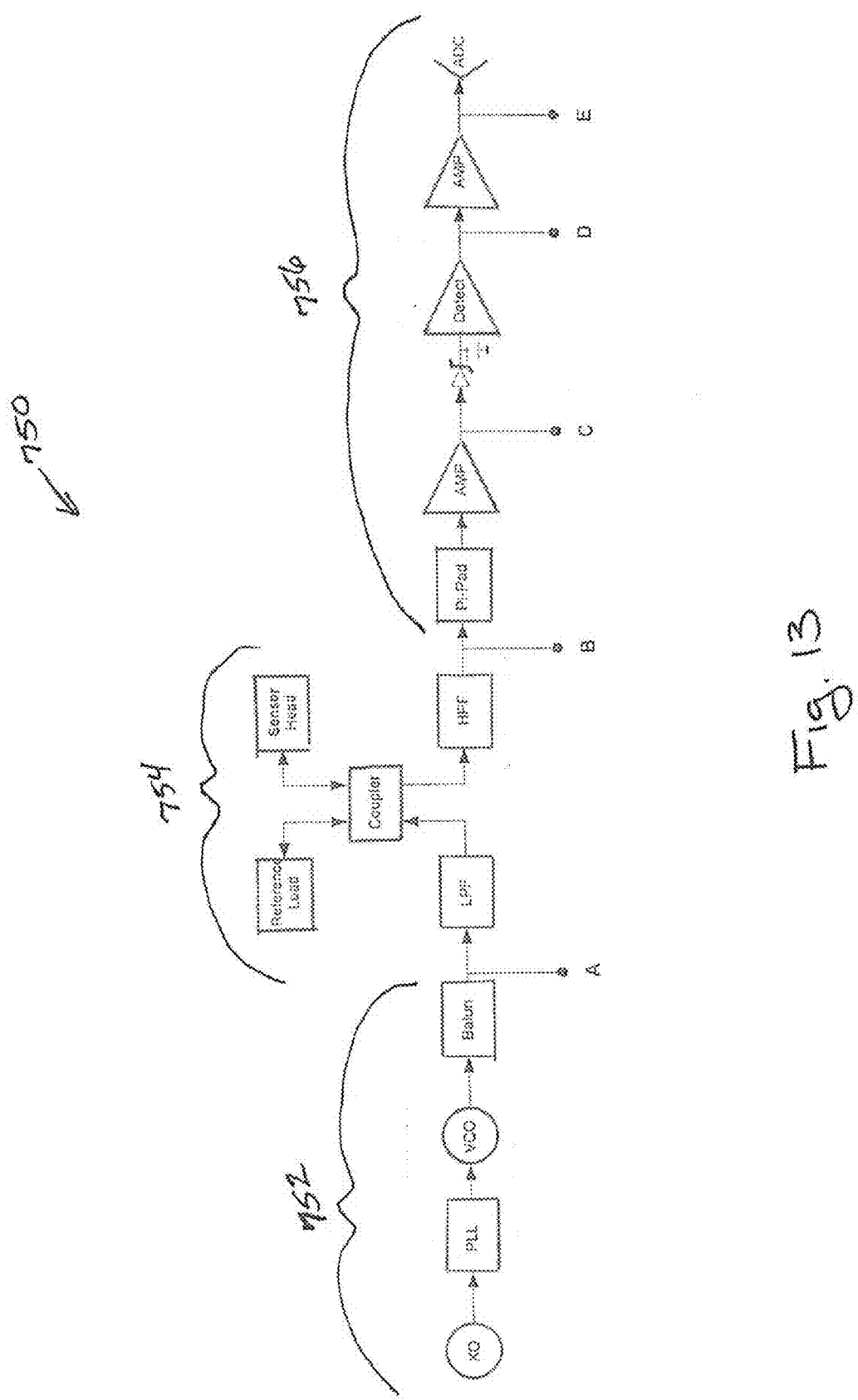
FIG. 13 depicts a sensing circuit topology that provides phase detection of a test signal applied to a sensor head tuned to resonance using an interferometer technique in an embodiment of the invention.

The second circuit topology 750 embodiment, as depicted in FIG. 13, uses an interferometer technique and includes an RF source 752, an interferometer network 754, and an envelope detection circuit 756. The RF source 752 provides the carrier signal to the interferometer at point A. The interferometer network 754 AM modulate the carrier signal in response to phase variations in the sensor head reflection coefficient resulting from seeds passing through the sensor. The modulated carrier is then provided to an envelope detection circuit 756 at point B. Within the envelope detection circuit 756 the carrier is provided to an RF amplifier gain stage and then to the input of a Schottky diode envelope detector at point C. The detector AM demodulates the carrier signal and provides the base band seed pulse response at point D where it is applied to the input of an operational amplifier. The operational amplifier removes any DC offset and provides further gain before the signal is sampled with an analog to digital converter at point E for further digital processing.

Figure 14:
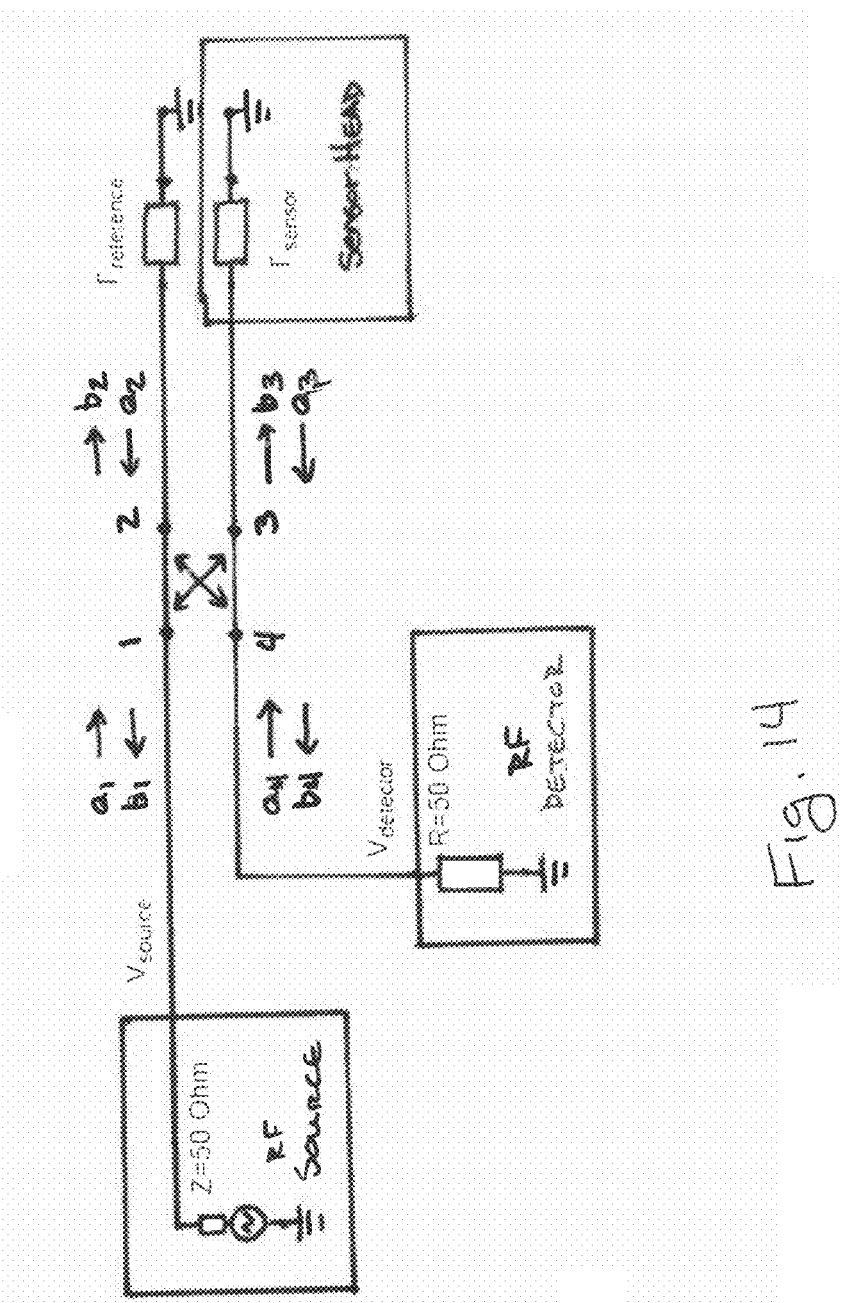
FIG. 14 depicts an interferometer circuit as utilized in an embodiment of the invention.

The interferometer 754 re-combines the out-of-phase signals from the sensor and the reference load and detects the amplitude of the resultant signal. The basic principal of an interferometer is shown in FIG. 14. In practice, a signal source is split and reflected off a reference load and a sensor head. The reflections are combined at the RF detector. The reference load can be chosen so that the two reflections are out-of-phase and nearly cancel at the detector when the sensor is in its unperturbed state. When a seed passes through the sensor, the cancellation at the detector will be disrupted and a change in signal amplitude will be sensed.

Environmental conditions could cause the resonant frequency of the sensor to vary or drift. The RF can be dithered to counter resonance drifts. Dithering is a function of the RF circuit that adds some form of phase or frequency modulation to the carrier signal generated by the RF source. This creates a broader band width signal that covers the range of frequencies over which the sensor resonance may vary due to various tolerances. By dithering the exciting RF field in frequency about the nominal resonant frequency, we can ensure that the true resonant frequency is within the bandwidth of the dithered signal. Because the sensitivity is highest at the resonant frequency, the envelope detection will ensure that only the response at the resonance frequency will dominate the detected signal. In another embodiment, a software algorithm could automatically set the output frequency to the sensor resonance based on training from the signal.

Reference is now made to an algorithm to facilitate functionality of the RF sensor embodiments disclosed herein. Implementing the algorithm to count seeds entails splitting the incoming signal into discrete pulses using a suitable threshold. Seed physical characteristics are approximately the same for the same type of seed, thus the pulse generated by each seed should have approximately the same width, height, shape, and subsequently, the same mean area under each pulse. Thus, estimating the area under the sensor signal should give reasonably accurate information about the number of seeds.

A histogram is then developed where the pulse areas show distinct peaks for pulses corresponding to one seeds, two seeds, etc. This statistical information is used to estimate the number of seeds in a cluster based on their area. The pulse areas are used to maintain the current statistical information by monitoring area statistics in a moving time window or monitoring area statistics over disjointed fixed time intervals. For example, the seed area and the knowledge peaks in the histogram tell us the statistical probability that the pulse is likely to be a single, a double, and so on.

In embodiments, the sensor RF signal is demodulated to give an analog signal which is digitized by an analog to digital converter. This digitized signal is communicated to the cab of the tractor through a bus that is standard on current equipment. Thus, the farmer receives real-time feedback during planting operations. Therefore, the embodiments disclosed herein are advantageous in that the seed sensors provide feedback in real-time which allows the farmer to immediately adjust the amount of seed being fed to the seed chute "on-the-fly." Thus, used is the minimum amount of seed resulting in the idealized yield. It further permits the optimum spacing of the seeds.

The following patents that relate to seed sensor devices are herein incorporated by reference in their entirety and constitute part of the disclosure herein: U.S. Pat. Nos. 4,782,282; 6,208,255; 6,346,888; 4,257,001; 4,246,469, and U.S. Patent Application 20120169353.

Having thus described several illustrative embodiments, it is to be appreciated that various alterations, modifications, and improvements will readily occur to those skilled in the art. Such alterations, modifications, and improvements are intended to be part of this disclosure, and are intended to be within the spirit and scope of this disclosure. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

The foregoing discussion is directed to radio frequency (RF) components and effects. It is understood that the disclosures above are equally applicable to electromagnetics generally, including microwave components and effects. Accordingly, terms such as RF cavity, RF sensor, RF probe, RF capacitance, RF circuits, RF signals, RF sources and RF fields apply more generally to electromagnetic cavities, sensors, probes, capacitance, circuits, signals, sources and fields, and also to microwave cavities, sensors, probes, capacitance, circuits, signals, sources and fields.

While the invention is amenable to various modifications and alternative forms, specifics thereof have been shown by way of example in the drawings and text. It should be understood, however, that the intention is not to limit the invention to the particular embodiments described. On the contrary, the intention is to cover all modifications, equivalents, and alternatives falling within the spirit and scope of the invention as defined by the appended claims.

It should be appreciated that various aspects of the subject matter discussed above may be implemented in any of numerous ways, as the subject matter is not limited to any particular manner of implementation. Examples of specific implementations and applications are provided primarily for illustrative purposes.

All of the features disclosed in this specification (including any accompanying claims, abstract and drawings), and/or all of the steps of any method or process so disclosed, can be combined in any combination, except combinations where at least some of such features and/or steps are mutually exclusive.

Each feature disclosed in this specification (including any accompanying claims, abstract and drawings) can be replaced by alternative features serving the same, equivalent or similar purpose, unless expressly stated otherwise. Thus, unless expressly stated otherwise, each feature disclosed is one example only of a generic series of equivalent or similar features.

For purposes of interpreting the claims for the present invention, it is expressly intended that the provisions of Section 112, sixth paragraph of 35 U.S.C. are not to be invoked unless the specific terms "means for" or "step for" are recited in the subject claim.

What is claimed is:

1. A method of counting seeds passing through a seed chute during agricultural planting operations, comprising:
    providing a sensor to attach to and surround the seed chute, the sensor creating a sensing plane across a diameter of the seed chute;
    connecting to the sensor an electronic circuit having an electromagnetic source, an interferometer, and an envelope detector;
    introducing an electromagnetic field in the sensor via the electromagnetic source, generating a fringing field penetrating the seed chute and creating a uniform sheet of electromagnetic field in the sensing plane;
    detecting a phase modulation of a signal reflected from the sensor as the electromagnetic field is perturbed by the passing seeds via the interferometer;
    modulating a carrier signal in response to phase variations in the sensor head reflection coefficient;
    providing the modulated carrier signal to an electromagnetic amplifier gain stage and then to the envelope detector;
    demodulating the carrier signal and providing a base band seed pulse response to an operational amplifier to remove any DC offset and providing further gain; and
    sampling the demodulated carrier signal with an analog to digital converter and processing the demodulated carrier signal.

2. The method of claim 1 wherein the step of generating a fringing field includes forming a resonant cavity and generating a resonant electromagnetic field in the sensing plane.

3. The method of claim 2 further including the step of including a material disposed within said resonant electromagnetic cavity to facilitate a shortened electromagnetic cavity, wherein the permittivity of the material is about 2 to about 100.

4. The method of claim 2 further including a material disposed adjacent to a probe within said resonant electromagnetic cavity to change a coupling between the probe and the resonant cavity thereby changing an amount of energy being transferred into the resonant cavity, wherein the permittivity of the material is about 2 to about 100.

* * * * *